United States Patent [19]

Leopold

[11] Patent Number: 5,346,505
[45] Date of Patent: Sep. 13, 1994

[54] EASILY EXCHANGEABLE CATHETER SYSTEM

[75] Inventor: Andrew R. Leopold, Sunnyvale, Calif.

[73] Assignee: Advanced Cardiovascular Systems, Inc., Santa Clara, Calif.

[21] Appl. No.: 920,795

[22] Filed: Jul. 28, 1992

Related U.S. Application Data

[63] Continuation of Ser. No. 712,088, Jun. 7, 1991, Pat. No. 5,154,725.

[51] Int. Cl.$^5$ ............................................. A61M 29/00
[52] U.S. Cl. ..................................... 606/194; 604/102; 604/160; 604/96
[58] Field of Search ...................... 606/192, 194, 195; 604/160, 161, 96, 102, 282; 128/657, 772

[56] References Cited

U.S. PATENT DOCUMENTS

| | | | |
|---|---|---|---|
| 4,748,982 | 6/1988 | Horzewski et al. | 604/102 |
| 4,943,278 | 7/1990 | Euteneuer et al. | 604/96 |
| 4,988,356 | 1/1991 | Crittenden et al. | 604/192 |
| 5,156,594 | 10/1992 | Keith | 604/96 |

*Primary Examiner*—Cary E. O'Connor
*Attorney, Agent, or Firm*—Crosby, Heafey, Roach & May

[57] ABSTRACT

A balloon dilatation catheter having a proximal tubular member formed of high strength materials such as stainless steel with an inner lumen for directing inflation fluid through the tubular member, a double lumen distal member which is secured to the distal end of the proximal tubular member with one of the lumens in the distal member being in fluid communication and axially aligned with the inner lumen of the proximal tubular member and the other lumen which is generally offset and parallel to the first inner lumen being adapted to slidably receive a guidewire and an inflatable balloon on the distal member. A proximal port in the proximal end of the second inner lumen is spaced at least 10 cm but not more than about 40 cm proximally from a distal port in the distal end of the catheter.

12 Claims, 1 Drawing Sheet

EASILY EXCHANGEABLE CATHETER SYSTEM

This is a continuation of the application Ser. No. 07/712,088 which was filed on Jun. 7, 1991, now U.S. Pat. No. 5,154,725.

BACKGROUND OF THE INVENTION

This invention generally relates to a catheter system tier intravascular procedures such as percutaneous transluminal coronary angioplasty (PTCA) which has the capability of being readily exchanged for another catheter without the need for guidewire extensions and exchange wires.

In classic PTCA procedures, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from the proximal end to turn the distal tip of the guiding catheter so that it can be guided into the coronary ostium. A dilatation catheter having a balloon on the distal end thereof and a guidewire slidably disposed within an inner lumen of the dilatation catheter are introduced into and advanced through the guiding catheter to the distal tip thereof. The distal tip of the guidewire is usually manually shaped (i.e. curved) by the physician or one of the attendants before the guidewire is introduced into the guiding catheter along with the dilatation catheter. The guidewire is first advanced out the distal tip of the guiding catheter, which is seated in the ostium of the patient's coronary artery, into the patient's coronary artery. A torque is applied to the proximal end of the guidewire, which extends out of the patient, to guide the curved or otherwise shaped distal end of the guidewire as the guidewire is advanced within the coronary anatomy until the shaped distal end of the guidewire enters the desired artery. The advancement of the guidewire within the selected artery continues until it crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the flexible, relatively inelastic balloon is inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can then be resumed therethrough.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); and U.S. Pat. No. 4,748,982 (Horzewski et al.) which are hereby incorporated herein in their entirety by reference thereto.

Recently, the assignee of the present invention, Advanced Cardiovascular Systems, Inc., introduced into the market place an improved dilatation catheter which is described and claimed in copending application Ser. No. 550,801 (Yock), filed Jul. 9, 1990 and U.S. Pat. No. 4,748,982 (Horzewski et al). This dilatation catheter has a short guidewire receiving sleeve or inner lumen extending through just the distal portion of the catheter. The sleeve extends proximally at least 10 cm, typically about 25 cm, from a first guidewire port in the distal end of the catheter to a second guidewire port in the side wall of the catheter. A slit is provided in the catheter wail which extends distally from the second guidewire port to a location proximal to the proximal end of the inflatable balloon. The structure of the catheter allows for the rapid exchange of the catheter without the need for an exchange wire or adding a guidewire extension to the proximal end of the guidewire.

The catheter design embodying the Yock and Horzewski et al. improvements has been widely praised by the medical profession and has been met with much success in the market place. Nonetheless, there are some inconveniences in its use. For example, the catheter shaft proximal to the proximal guidewire port contained both an inflation lumen and a stiffening member and in order to maintain a relatively low profile the inflation lumen frequently the catheter did not have a sufficiently large diameter for rapid inflation and deflation of the balloon. Additionally, it has been found that guidewires had a tendency to hang up on the notch in the catheter wail forming the proximal guidewire port, making withdrawal difficult.

What has been needed and heretofore unavailable is an intravascular catheter system which allows for the rapid exchange of a guidewire while providing for short inflation/deflation times and for a smooth insertion and withdrawal of a guidewire therefrom. The present invention satisfies these and other needs.

SUMMARY OF THE INVENTION

This invention is directed to an balloon dilatation catheter which can be advanced over a guidewire into a patient's vasculature and can be readily withdrawn from the patient and removed from the guidewire without the need for either replacing the guidewire with an exchange wire or for attaching a guidewire extension to the proximal end of the guidewire.

The dilatation catheter of the invention has an elongated body with a relatively high strength proximal tubular member having an inner lumen extending between the proximal and distal ends of the member and a multilumen distal member which is more flexible and shorter than the proximal tubular member, which is secured to the distal end of the proximal tubular member and which has an inflatable balloon adapted to dilate atherosclerotic plaque.

One of the inner lumens in the multilumen distal member is adapted to direct inflation fluid therethrough and is in fluid communication with the inner lumen of the proximal tubular member at one end and with the interior of the inflatable member on the other end. The inner lumen of the proximal tubular member and the inflation lumen multilumen distal member are dimensioned to provide relatively short inflation and deflation times for the dilatation balloon on the distal member. The second inner lumen in the multilumen distal member has proximal and distal ports in the proximal and distal ends thereof and is adapted to slidably receive a guidewire, The second guidewire receiving lumen of the multilumen distal member is generally parallel to and offset from the axis of the inflation lumen in the multilumen distal member but a tubular extension distal to the inflation port of the inflation lumen within the interior of the balloon generally defines the guidewire receiving lumen therein to the distal end the multilumen distal member. The length of the guidewire receiving lumen in the distal member, i.e. the distance between the proximal guidewire port and the distal guidewire port, should be greater than about 10 cm but not greater than about 40 cm and preferably is about 15 to about 30 cm so that the portion of the guidewire extending out the proximal guidewire port is disposed within the guiding catheter during an angioplasty procedure.

A relatively inelastic inflatable balloon is provided on the multilumen distal member with the distal end of the balloon sea jingly bonded about the tubular extension of the multilumen distal member which extends through the interior of the balloon. The tubular extension defines and continues the second, guidewire receiving inner lumen to the distal end of the multilumen distal member.

In a presently preferred embodiment of the invention, the guidewire receiving inner lumen in the multilumen distal member is defined at least in part by a wall which has a slit therein extending from the first guidewire port to a location proximal to the proximal end of the balloon. The entry angle into the proximal port with respect to the axis of the guidewire receiving inner lumen is very small, generally less than about 30 degrees, preferable less than about 15 degrees. The very small angle of attack generally provides a smooth entry and withdrawal of the guidewire from the guidewire receiving inner lumen and thereby prevents the guidewire from being hung up at the proximal port.

The proximal tubular member is formed of high strength materials such as stainless steel and alloys such as NiTi alloys which have superelastic properties to provide a high level of pushability. Preferably, the proximal metallic tubular member has a coating or jacket formed out of nonthrombogenic materials such as plastic. e.g. polyethylene, which is secured to the exterior thereof by suitable means such as heat shrinking or an adhesive.

The multilumen distal member is may be formed from suitable thermoplastic resins such as polyethylene. In a presently preferred embodiment, the portion of the distal member having two lumens is formed of a mixture of high density and low density (50%/50%) polyethylene. The tubular extension of the multilumen distal member extending through the interior of the balloon, which defines the guidewire receiving lumen, is formed from 100% high density polyethylene.

The balloon is preferably formed of thermoplastic material such as polyethylene and polyethylene terephthalate which are formed to generate high strength and biaxially orientation.

The catheter of the invention provides improved pushability with smooth advancement of the catheter over the guidewire, while retaining a relatively low profile and easy exchangeability. These and other advantages of the invention will become more apparent from the following detailed description thereof when taken in conjunction with the accompanying exemplary drawings.

DETAILED DESCRIPTION OF THE INVENTION

Figure 1:
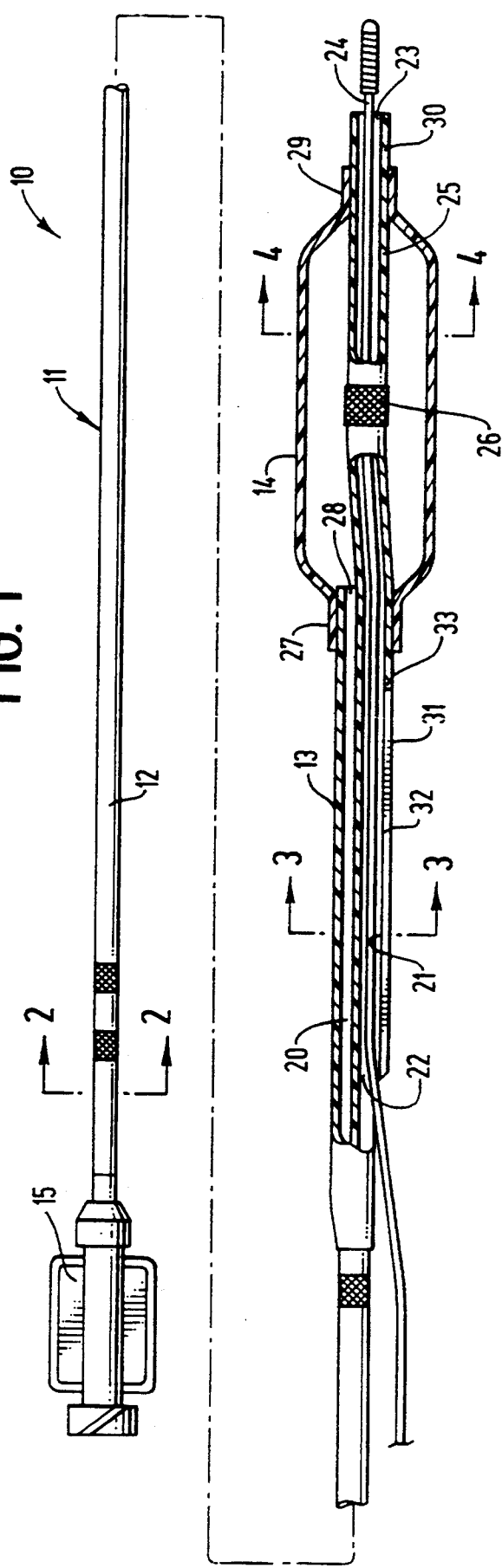
FIG. 1 is an elevational view, partially in section, of a dilatation catheter having features of the invention.
Figure 4:
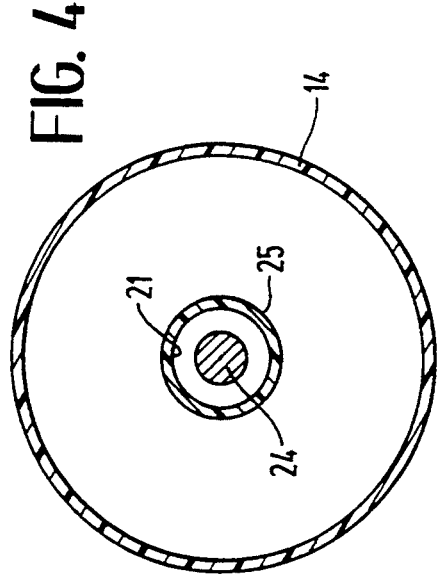
FIG. 4 is a transverse cross section view of the dilatation catheter shown in FIG. 1 taken along the lines 4—4.

Reference is made to FIGS. 1-4 which illustrate a dilatation catheter which embodies features of the invention. The dilation catheter 10 generally includes an elongated catheter body 11 having a proximal high strength tubular member 12 and a multilumen distal member 13, an inflatable relatively inelastic balloon 14 on the multilumen distal section of the catheter body and an adapter 15 on the proximal end of the proximal tubular member.

Figure 2:
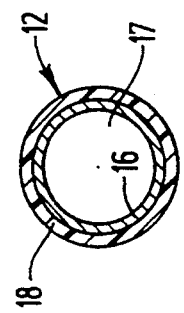
FIG. 2 is a transverse cross sectional view of the dilatation catheter shown in FIG. 1 taken along the lines 2—2.

As shown in FIG. 2, the proximal high strength tubular member 12 is formed of metallic hypotubing 16 having an inner lumen 17 adapted to direct inflation fluid from the adapter 15 to the interior of the balloon 14. An outer plastic jacket 18 is heat shrunk onto the exterior of the hypotubing 16. The proximal tubular member 12 has an outer diameter which may range from about 0.02 to about 0.03 inch (0.51–0.76 mm) and is typically about 0.025 inch (0.64 mm) over most of its length. The distal portion of the hypotubing 16 may be tapered to increase the flexibility in that region by drawing or the like. It is preferred to draw the tube with a mandrel of the same outer diameter as the original inner diameter thereof to maintain an inflation lumen within the proximal tubular member having an essentially constant diameter. The wall thickness of the hypotubing 16 may be about 0.001 to 0.005 inch (0.025–0.13 mm) depending upon the flexibility and pushability required or desired in the final product.

Figure 3:
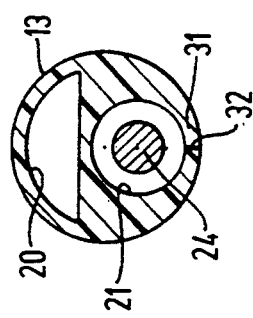
FIG. 3 is a transverse cross sectional view of the dilatation catheter shown in FIG. 1 taken along the lines 3—3.

The multilumen distal section 13 of the catheter body 11, as illustrated in FIG. 3, has two inner lumens 20 and 21 extending therein. The first inner lumen 20 is an inflation lumen having a D-shaped transverse cross-sectional shape which is in fluid communication with the inner lumen 17 of the proximal tubular member 12 and is generally axially aligned therewith. The second inner lumen 21 has a circular transverse cross-sectional shape, is adapted to receive a guidewire receiving and is generally offset from the inflation lumen 20 and parallel thereto.

The distal end of the proximal tubular member 12 is preferably truncated so that it easily interfits into inflation lumen 21 at the proximal end of the distal multilumen distal section 13. The D-shaped cross sectional area of the inflation lumen 20 is generally as large or larger than the circular cross sectional area of the inflation lumen 18 in the proximal tubular member 12 to facilitate the rapid transfer of inflation fluid to and from the interior of the balloon 14.

The guidewire receiving lumen 21 has a proximal guidewire port 22 at the proximal end thereof and a distal guidewire port 23 at the distal end thereof. The proximal port 22 is aligned with the longitudinal axis of the guidewire lumen 21 to allow a guidewire 24 straight access to the inner lumen 21 so there is little chance than the guidewire will become bound up at this port upon the movement of the guidewire within the inner lumen.

A tubular extension 25 of the multilumen distal section 13, which contains part of the guidewire receiving inner lumen 21, extends through the interior of the balloon 14 and is provided with a radiopaque marker 26 on the exterior thereof at the mid-point of the balloon 14.

The proximal end 27 of the balloon 14 is bonded by a suitable adhesive to the exterior of the multilumen distal section 13 at a location proximal to the inflation port 28 at the distal end of the inner lumen 20, The distal end 29 of the balloon 14 is sealingly bonded by an adhesive to the distal end 30 of the tubular extension 25. A presently preferred adhesive is an cyanoacrylate based adhesive such as Loctite TM 405 adhesive.

The inner diameters of the guidewire receiving lumen 21 and the guidewire ports 22 and 23 at the proximal and distal ends of the distal section 13 are large enough to facilitate the sliding of a guidewire 24 therein but generally should not be more than about 0.004 inch (0.1 mm) larger than the outer diameter of the guidewire. The wall 31 of the distal section 13 which forms in pan the inner lumen 21 is provided with a slit 32 from the proximal port 22 to a location 33 proximally adjacent to the proximal end 27 of the balloon 14 to facilitate the removal of the catheter from the guidewire 24 as described by Horzewski et al. incorporated herein.

The distal section of the catheter body 11 can be formed by conventional techniques, e.g. extruding, from materials already found useful in intravascular catheters such a polyethylene, polyimide, polyvinyl chloride, polyesters and composite materials such as described in U.S. Pat. No. 4,981,478 (Evard et al.) which is incorporated herein by reference. The balloon 14 may be formed from suitable materials such as polyethylene, polyethylene terephthalate and ionomers such as Suryln, particularly from such materials having biaxially orientation. The distal member 13 of the catheter 10 must be of sufficient thickness and strength so that it can be pushed over a guidewire to the desired location within the patient's blood vessel. The proximal metallic tubular section may be formed of high strength materials such as stainless steel (304), superelastic Nitinol such as described and claimed in copending application Ser. No. 07/629,381, filed Dec. 18, 1990, entitled "Superelastic Guiding Member" which is incorporated herein in its entirety, and other materials with similar properties. Preferably, the proximal metallic tubular member has an outer jacket of plastic materials such as a high density polyethylene which has been heat shrunk onto the exterior of the tubular member or otherwise bonded thereto by a suitable adhesive such as an cyanoacrylate-based adhesive.

The diameter of the guidewire receiving inner lumen 14 in the distal section 13 to a large extent is determined by the size of the guidewire to be disposed therein and generally will be sufficiently large to readily accommodate the guidewire and to allow it to be slidably disposed therein. Generally the diameter of the inner lumen 14 will be about 0.012 to about 0.225 inch (0.3–0.64 mm). The diameters of guidewires for coronary use can vary from about 0.08 to about 0.2 inch (0.2–0.51 mm) in diameter, and the inner diameter of the guidewire receiving inner lumen 14 of the catheter 10 should be about 0.001 to about 0.005 inch (0.025–0.127 mm) larger than the diameter of the guidewire. The catheter body 11 is sufficiently long to extend from outside the proximal end of a guiding catheter, which likewise extends out of the patient, to a stenosis to be treated within the patient's vascular system (or other desired location therein), e.g. from about 100 to about 150 cm when a Seldinger approach through the femoral artery is employed to introduce the catheter into the patient's vasculature.

The dilatation catheter 10 of the invention is utilized in the manner generally described in Horzewski et al. which has been incorporated herein. A guiding catheter (not shown) is first introduced into the patient's vasculature with the distal tip seated within the ostium of the desired coronary artery of a patient in a conventional fashion as previously described. The proximal end of the guidewire 24 is backloaded through the distal guidewire port 23 into the guidewire receiving inner lumen 21 until the proximal end of the guidewire extends out the proximal port 22. The guidewire 24 and dilatation catheter 10 are advanced into and through the guiding catheter to the distal end thereof. The guidewire 24 is first advanced out the distal end of the guiding catheter into the patient's coronary artery until the distal end of the guidewire crosses the stenosis to be dilated. The dilatation catheter 10 is then advanced out of the distal end of the guiding catheter into the patient's coronary artery over the previously positioned guidewire until the balloon 14 on the dilatation catheter is in positioned across the stenosis to be dilated. If after the dilatation, or for that matter any time during the angioplasty procedure, another size catheter is needed, e.g. one with a larger balloon, the in-place catheter is withdrawn from the patient by pulling on the proximal end thereof which extends out of the proximal end of the guiding catheter which in turn extends out of the patient. When the proximal port 22 extends out the proximal end of the guiding catheter the catheter 10 can be peeled off the guidewire 24 through the slit 32 therein. When the distal end of the dilatation catheter 10 exits the proximal end of the guiding catheter, the guidewire 24 can be held manually distal thereto and then the dilatation catheter 10 can be pulled off the proximal end of the guidewire. The replacement catheter, having a short guidewire receiving inner lumen as the catheter removed from the guidewire, is mounted onto the guidewire by advancing the proximal end of the guidewire through the distal port in the replacement catheter and advanced through the guidewire receiving inner lumen and out the proximal guidewire port. The replacement dilatation catheter is then advanced through the guiding catheter over the in-place guidewire and into the patient's coronary artery wherein the balloon on the distal end of the replacement catheter is inflated to dilate the stenosis within the patient's coronary artery.

While the invention has been described herein in terms of certain preferred embodiments, those skilled in the art will recognize that various modifications can be made. For example, the multilumen distal member may be formed of concentrically arranged tubular members such as described in copending application Ser. No. 07/700,617, filed on May 15, 1991, entitled "Low Profile Dilatation Catheter" (Sirban et al.). Other modifications and improvements can be made to the present invention without departing from the scope thereof.

What is claimed is:

1. A readily exchangeable balloon dilatation catheter comprising:
   a) an elongated, high strength proximal tubular member which is formed of hypotubing, which has proximal and distal ends and which has an inner lumen extending therein;

b) a flexible distal tubular member which is secured to the distal end of the high strength proximal tubular member, which has an inflation lumen extending longitudinally therein with a proximal end in fluid communication with the inner lumen of the high strength proximal tubular member and a distal end with an inflation port therein, and which has a guidewire receiving inner lumen extending longitudinally between a first guidewire port and a distal guidewire port in the distal end thereof, the proximal guidewire port being spaced longitudinally from the distal port in the distal end and having an entry angel of not more than about 30°; and c) an inflatable, relatively inelastic balloon on the distal tubular member having a distal end sealingly bonded about the distal end of the distal tubular member and an interior which is in fluid communication with the inflation lumen through the inflation port thereof.

2. The dilation catheter of claim 1 wherein the distal end of the proximal tubular member is truncated and interfits into the inflation lumen in the distal member.

3. The dilation catheter of claim 2 wherein the distal tubular member has a wall which defines in part the guidewire receiving inner lumen and which has a slit therein extending from the proximal guidewire port to a location proximally adjacent the inflatable balloon.

4. The dilation catheter of claim 1 wherein the hypotubing of the proximal tubular member is formed from a material selected from the group consisting of stainless steel and a superelastic Nitinol alloy.

5. The dilation catheter of claim 1 wherein the hypotubing of the proximal tubular member is provided with a plastic jacket.

6. The dilation catheter of claim 1 wherein the proximal guidewire port is space proximally from the distal guidewire port a distance not greater than 40 cm.

7. The dilation catheter of claim 1 wherein the proximal guidewire port is space proximally from the distal guidewire port a distance of about 15 to about 30 cm.

8. The dilation catheter of claim 1 wherein the proximal tubular member is tapered in a distal portion thereof proximal to the distal tubular member to provide increased flexibility in the distal portion of the proximal tubular member.

9. The dilation catheter of claim 1 wherein the transverse cross sectional area of the inner lumen of the proximal tubular member is essentially the same as the transverse cross sectional area of the inflation lumen in the distal tubular member.

10. The dilation catheter of claim 1 wherein the inflation lumen of the proximal tubular member is axially aligned with the inflation lumen within the distal tubular member.

11. The dilation catheter of claim 1 wherein the transverse shape of the inflation lumen is D-shaped.

12. The dilation catheter of claim 1 wherein the proximal guidewire port has an entry angle with respect to a longitudinal axis of the guidewire receiving inner lumen of less than about 15°.

* * * * *